United States Patent
Kushiku et al.

(10) Patent No.: US 7,553,367 B2
(45) Date of Patent: Jun. 30, 2009

(54) METHOD OF MAKING A DIL-LYSINE MONOSULFATE TRIHYDRATE CRYSTAL

(75) Inventors: Takeshi Kushiku, Kawasaki (JP); Dave Steckelberg, Eddyville, IA (US); Toshiya Tanabe, Tokyo (JP); Jirou Haga, Kawasaki (JP); Shinya Fujiki, Kawasaki (JP); Kisho Suzuki, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 357 days.

(21) Appl. No.: 11/423,969

(22) Filed: Jun. 14, 2006

(65) Prior Publication Data

US 2006/0281945 A1 Dec. 14, 2006

Related U.S. Application Data

(60) Division of application No. 10/736,511, filed on Dec. 17, 2003, now Pat. No. 7,161,029, and a continuation of application No. PCT/JP2004/019465, filed on Dec. 17, 2004.

(51) Int. Cl.
*C30B 7/08* (2006.01)
(52) U.S. Cl. .............. 117/68; 117/69; 117/70
(58) Field of Classification Search .......... 117/68, 117/69, 70
See application file for complete search history.

(56) References Cited

U.S. PATENT DOCUMENTS

| 3,987,092 | A | 10/1976 | van der Linden et al. |
| 4,256,917 | A | 3/1981 | Takayanagi et al. |
| 4,399,304 | A | 8/1983 | Matsuishi et al. |
| 4,670,261 | A | 6/1987 | Samejima et al. |
| 5,689,001 | A | 11/1997 | Hasegawa et al. |
| 6,329,548 | B1 * | 12/2001 | Hasegawa et al. ........... 562/562 |
| 6,617,444 | B1 | 9/2003 | Mori et al. |
| 2005/0132947 | A1 | 6/2005 | Kushiku et al. |

OTHER PUBLICATIONS

Roth, F.X., et al., "Biological Efficiency of L-Lysine Base and L-Lysine Sulphate Compared with L-Lysine HCl in Piglets," Agribio. Res. 1994;47(2):177-186.
Aketa, K., et al., "Stereochemical Studies. XL. A Biomimetic Conversion of L-Lysine into optically Active 2-Substituted Piperidines. Synthesis of D- and L-Pipecolic Acid, and (S)(+)-Coniine from L-Lysine," Chem. Pharm. Bull. 1976;24(4):621-631.
Roth et al., "Biological Efficiency of L-Lysine Base and L-Lysine Sulphate Compared with L-Lysine HCl in Piglets," Agribio. Res. 1994;47(2):177-186.
International Search Report for PCT App. No. PCT/JP2004/019465 (Apr. 26, 2005).
International Preliminary Report on Patentability and Written Opinion of the International Searching Authority for PCT App. No. PCT/JP2004/019465 (Jun. 29, 2006).
Official Office Action from Russian Patent Office in Application No. 2006125407 (PCT/JP2004/019465, citing SU383281A (equivalent to US Patent 3,987,092, cited above).

* cited by examiner

*Primary Examiner*—Robert M Kunemund
(74) *Attorney, Agent, or Firm*—Shelly Guest Cermak; Cermak Kenealy; Vaidya & Nakajima LLP

(57) ABSTRACT

A diL-lysine monosulfate trihydrate crystal which has a large tabular form and is more easily separable from the mother liquor is described. The crystal is obtained by a novel process wherein crystallization is conducted at a lower temperature.

24 Claims, 13 Drawing Sheets

METHOD OF MAKING A DIL-LYSINE MONOSULFATE TRIHYDRATE CRYSTAL

This application claims priority as a divisional to U.S. application Ser. No. 10/736,511, filed Dec. 17, 2003 now U.S. Pat. No. 7,161,029, and as a comtinuation to PCT Application No. PCT/JP2004/019465, filed Dec. 17, 2004, both under 35 U.S.C. §120. The entireties of both are incorporated by reference.

BACKGROUND OF THE INVENTION

1. Field of the Invention

The present invention relates to L-lysine sulfate crystals and methods for making the crystals, and more specifically to diL-lysine sulfate crystals with crystal water incorporated into the structure, and a method of making these crystals in larger quantities which are readily separable from the mother liquor. Finally, the present invention relates to products containing L-lysine made by the above novel method.

2. Brief Description of the Related Art

L-lysine is one of the essential amino acids and is widely used in the pharmaceutical and agricultural industries as a nutrition regulator and feed additive, among other uses. It circulates primarily as L-lysine hydrochloride (www.ajinomoto.co.jp/ajinomoto/A-life/amino science/siryou/lijin.html). When in the form of diL-lysine sulfate, feed effects equivalent to those of L-lysine hydrochloride are seen (Roth et al., 1994:Biological Efficiency of L-Lysine Base and L-Lysine Sulphate Compared with L-Lysine HCl in Piglets; Agribio. Res. 47(2):177-186 (1994)).

Crystals of diL-lysine sulfate are known to contain anhydrous diL-lysine sulfate (Aketa et al., Stereo chemical studies XL A biomimetic conversion of L-lysine into optically active 2-substituted; Chem. Pharm. Bull. 24(4):623-31 (1976)). Therefore, alcohol is often added to the diL-lysine sulfate aqueous solution to enable production of anhydrous diL-lysine sulfate crystals. Because the added alcohol must be removed from the resulting crystals, an extra purification step must be added to the process, further reducing the yield of crystals. See Aketa et al.

Anhydrous diL-lysine sulfate crystals are known to be highly soluble in water, which also contributes to the low yields of crystals. As a result, the high concentration of crystals in the mother liquor causes a decreased rate of crystallization. The small amounts of crystals that are eventually obtained are very fine and small, which causes a difficult separation from the mother liquor, further exacerbating the low yield problem.

Therefore, there is clearly a need in the art for improved methods of obtaining pure and highly separable L-lysine crystals. As L-lysine is such an important component in products for many different industries, highly efficient methods for crystallizing and purifying L-lysine are clearly needed in the art.

The present invention describes a novel method for crystallization and purification of L-lysine that is highly efficient, provides significantly increased yields, and results in easier and more efficient separation of the product crystals from the mother liquor. The present invention also describes a novel crystal form of L-lysine sulfate.

SUMMARY OF THE INVENTION

The present invention describes a technique for crystallizing diL-lysine monosulfate trihydrate, and the resulting crystals, which are superior for separability and high yields, among other superior qualities.

According to a first aspect of the invention, a method of producing a diL-lysine monosulfate trihydrate crystal from a solution is described, comprising mixing a lysine solution with sulfuric acid at a temperature of between approximately −10° C. and approximately 35° C., allowing crystals to form, and recovering the crystals.

According to another aspect of the present invention, a method of producing diL-lysine monosulfate is described, comprising mixing a lysine solution with sulfuric acid at a temperature of between approximately −10° C. and approximately 35° C., allowing crystals to form, recovering the crystals, and drying crystals to remove the crystal water, and collecting diL-lysine sulfate is described.

According to a further aspect of the present invention, a diL-lysine monosulfate trihydrate crystal is described which is characterized by having peaks at diffraction angles 2θ of 16.6° and 17.0° in powder X-ray diffraction.

According to an even further aspect of the present invention, a method of producing a diL-lysine monosulfate trihydrate crystal from an solution is described, comprising mixing a lysine solution with sulfuric acid at a temperature above approximately 40° C., and allowing crystals to form, then lowering the temperature until it is between approximately −10° C. and approximately 35° C., and allowing crystals to form, and recovering the crystals.

According to an even further aspect of the present invention, a method of producing a diL-lysine monosulfate trihydrate crystal is described, comprising concentrating an aqueous diL-lysine monosulfate trihydrate solution by evaporation, and allowing a crystal to form, and recovering said crystal.

According to an even further aspect of the present invention, a method of producing a diL-lysine monosulfate trihydrate crystal is described comprising preparing an aqueous diL-lysine monosulfate trihydrate solution at a temperature above approximately 40° C., lowering the temperature until it is between approximately −10° C. and approximately 35° C., and allowing crystals to form, and recovering said diL-lysine monosulfate trihydrate crystal.

According to an even further aspect of the present invention, a method of producing a diL-lysine monosulfate trihydrate crystal is described comprising adding a poor solvent to an aqueous diL-lysine monosulfate trihydrate solution, and allowing a crystal to form, and recovering said crystal.

According to an even further aspect of the present invention, a method of producing a diL-lysine monosulfate trihydrate column crystal is described comprising preparing a slurry of diL-lysine monosulfate plate crystals at a temperature above approximately 40° C., lowering the temperature until it is between approximately −10 to 35° C., and allowing crystals to form, and recovering said crystals.

According to an even further aspect of the present invention, a method of producing diL-lysine sulfate is described comprising concentrating an aqueous diL-lysine monosulfate trihydrate solution by evaporation, and allowing a crystal to form, recovering said crystal, drying said crystal to remove the crystal water, and collecting said diL-lysine sulfate.

According to an even further aspect of the present invention, a diL-lysine monosulfate trihydrate crystal is described.

According to an even further aspect of the present invention, a diL-lysine monosulfate trihydrate crystal is described that is produced by the process described above.

According to an even further aspect of the present invention, a composition containing L-lysine, prepared by the above-described process, followed by a drying step.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the invention, given only by way of example, and with reference to the accompanying figures, in which.

DESCRIPTION OF THE PREFERRED EMBODIMENTS

The present invention describes a novel crystallization technique and purification process, as well as novel crystals of L-lysine sulfate for use in any application in which L-lysine is currently used, such as feed additives or nutritional supplements. More specifically, the present invention describes the formation of novel diL-lysine monosulfate trihydrate crystals through a novel purification process. The present invention describes how varying, and particularly lowering, the crystallization temperature when conducting crystallization results in the precipitation of novel diL-lysine monosulfate trihydrate, in addition to the crystals of anhydrous diL-lysine sulfate.

The novel diL-lysine monosulfate trihydrate crystals are advantageous over anhydrous diL-lysine sulfate crystals because they are larger and more readily separable from the mother liquor. Furthermore, due to lower solubility in water, a higher crystallization yield results, and since diL-lysine monosulfate trihydrate crystals incorporate water into the crystals as crystal water, an improved crystallization yield can be anticipated due to a reduction in the quantity of solvent used in crystallization.

Figure 1:
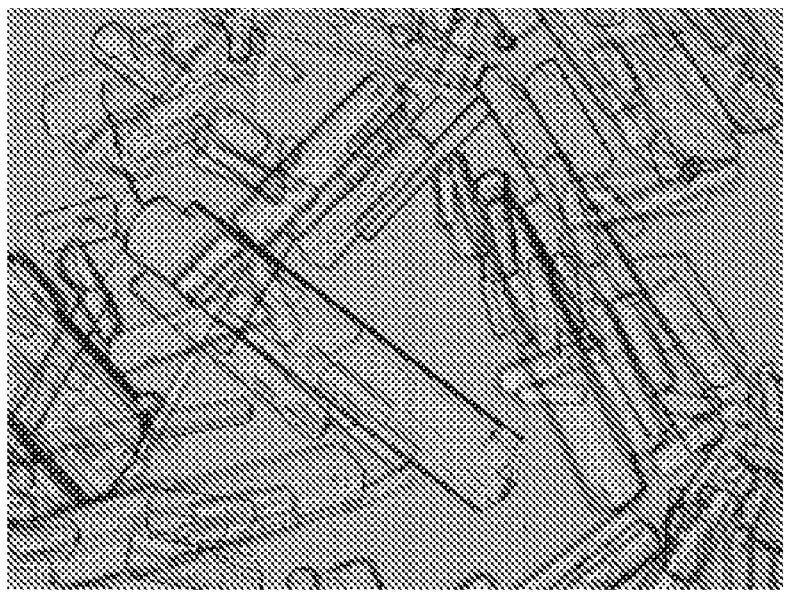
FIG. 1 illustrates crystals of diL-lysine monosulfate trihydrate (microphotograph).
Figure 2:
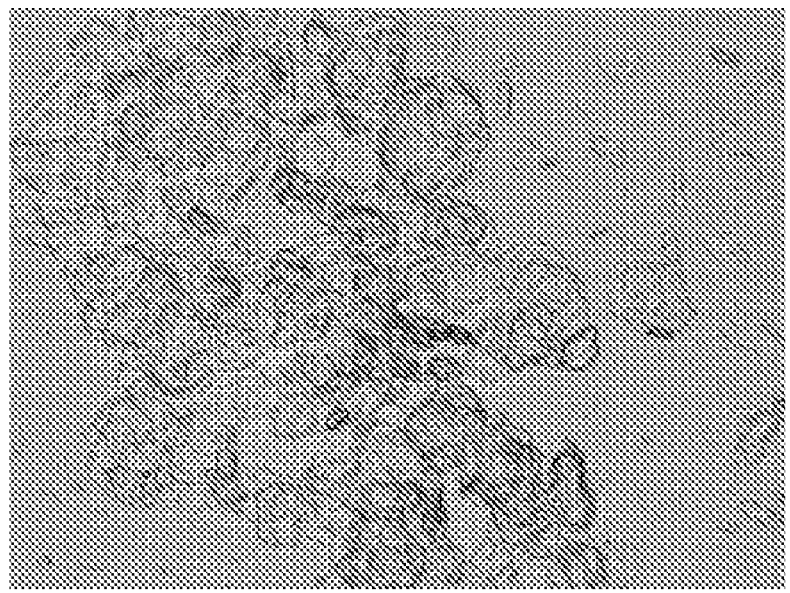
FIG. 2 illustrates crystals of anhydrous diL-lysine sulfate (microphotograph).

The diL-lysine monosulfate trihydrate crystals of the present invention have improved size and general form rendering them more easily separable from the mother liquor. FIG. 1 depicts the novel diL-lysine monosulfate trihydrate crystals, shown in the form of large tabular crystals. As shown in FIG. 1, these crystals are larger, tabular, and column-like. These larger crystals are more readily separable from the mother liquor during the separation step subsequent to crystallization. FIG. 2 shows, for comparison, the anhydrous diL-lysine sulfate crystals, which are clearly smaller and form in clumps (plate crystals), making them difficult to separate from the mother liquor, and causing lower yields.

The diL-lysine monosulfate trihydrate crystals of the present invention have water incorporated into the crystals, which enables their preferred form, size, and renders them more readily separable. Preferably, the crystals have 3 moles of water incorporated into the crystal lattice, resulting in a diL-lysine monosulfate trihydrate crystal.

The starting material for the novel crystallization method is in the form of a lysine solution (a solution containing L-lysine as a solute), preferably a diL-lysine sulfate aqueous solution. Preferably, the solution is over-saturated with diL-lysine sulfate, which enables the beginning of crystallization to occur. The diL-lysine sulfate solution that serves as a starting material may be prepared by any method known to those of skill in the art. The preferred method of obtaining the starting solution is to cause accumulation of diL-lysine sulfate in a culture solution as a result of fermentation. Japanese Unexamined Patent Publication (KOKAI) Heisei No. 5-30985 and Heisei No. 5-244969 teach exemplary methods of accumulating diL-lysine sulfate in a culture solution by fermentation. The crystallization process can be started directly from this fermentation broth by evaporating, followed by cooling. Alternatively, another possible method of obtaining the starting solution includes obtaining diL-lysine and sulfuric acid from commercial sources and mixing them in an aqueous solution.

The concentration of the diL-lysine sulfate solution which serves as a starting material can be adjusted for crystallization by methods known in the art. Typically, the solution should be over-saturated. Methods for determining formulation of the starting solution, including parameters such as concentration, temperature, and solubility are known in the art. As a guideline, the concentration need only be greater than the solubility of the diL-lysine sulfate. In one embodiment, if the crystallization temperature is 20° C., the solubility of diL-lysine sulfate at his temperature is 102.9 g/100 g water. Thus, the concentration of the diL-lysine sulfate in the crystallization starting material solution would be adjusted to 102.9 g/100 g water or greater. Adjusting the concentration may be accomplished by known methods in the art, for example, by pressure reduction or evaporation. However, any known method for adjusting the concentration to achieve over-saturation may be used.

Figure 3:
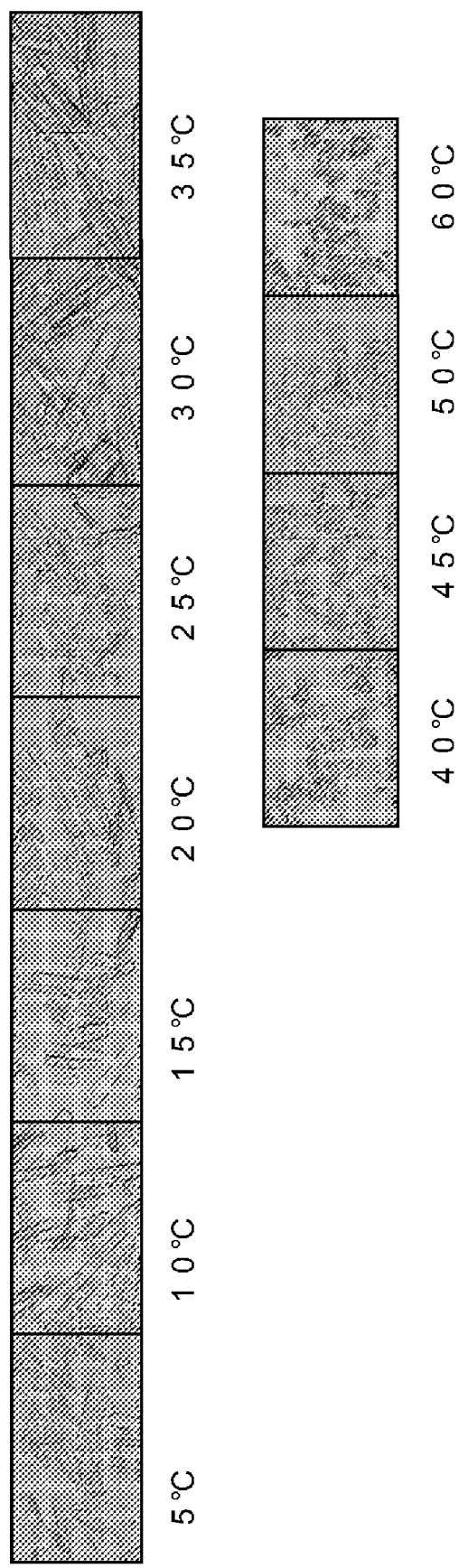
FIG. 3 illustrates crystals precipitated out of an aqueous solution of diL-lysine sulfate at various temperatures (microphotograph).

To obtain the larger, more readily separable diL-lysine monosulfate trihydrate crystals of the present invention, one may use the novel crystallization process of the present invention. The method of the present invention includes either beginning the crystallization at a temperature of between −10° C. and 35° C., or beginning at a higher temperature and subsequently lowering the temperature until it is in the above-desired range. These temperatures are approximate and may vary plus or minus 5° C. It was discovered that reducing the temperature of the starting material resulted in precipitation of the diL-lysine monosulfate trihydrate from the aqueous solution which results in the larger crystalline form. FIG. 3 depicts the form of the crystals when precipitated at varying temperatures from 5° C. to 60° C. at 5° C. intervals. As can be seen over the temperature range, the diL-lysine monosulfate trihydrate crystals which form below 35° C. are larger, more tabular and column-like. Over 40° C., the diL-lysine sulfate crystals which form are plate (small and in clumps). Therefore, the method of the present invention includes a crystallization step in which the temperature is preferably equal to or lower than approximately 35° C., more preferably below approximately 30° C., and even more preferably below approximately 25° C., and even more preferably below approximately 20° C. Most preferably, the temperature for crystallization is approximately 10° C. To enable the process, seed crystals of diL-lysine monosulfate trihydrate may be added to the starting material solution.

Specifically, the crystallization may be carried out by any of the following steps: (1) mixing a lysine solution with sulfuric acid at a temperature of between approximately −10° C. and approximately 35° C., and allowing the crystals to form, (2) mixing a lysine solution with sulfuric acid at a temperature above approximately 40° C., and allowing crystals to form, and (3) preparing an aqueous diL-lysine monosulfate trihydrate solution at a temperature above approximately 40° C.

Furthermore, in another embodiment, the crystals may be precipitated as anhydrous diL-lysine sulfate crystals at a temperature of 40° C. or greater, followed by lowering the temperature to 35° C. or below. In this way, diL-lysine monosulfate trihydrate crystals of the present invention are obtained through conversion into diL-lysine monosulfate trihydrate crystals. This method was advantageous in that the elimination of impurities through rearrangement was accomplished.

In addition, the crystallization may be conducted as follows.

The crystals may be precipitated by concentrating an aqueous diL-lysine monosulfate trihydrate solution by evaporation. The aqueous diL-lysine sulfate monosulfate trihydrate solution may be prepared by solving diL-lysine sulfate in water or adding sulfuric acid to an aqueous solution of a L-lysine salt other than sulfate. The concentration of diL-lysine monosulfate trihydrate is not particularly limited, but a saturated solution is preferable. The pH of the solution is not limited provided that the crystals precipitate, but is usually approximately 5.0 to 7.0. The evaporation may be conducted by an ordinary method. The pressure may be ordinary pressure or reduced pressure (usually 2640 to 4000 Pa). The temperature may be ordinary temperature or heat may be applied (usually 40.0 to 60.0° C.). The evaporation is preferably conducted under reduced pressure.

The crystals may be precipitated by adding a poor solvent to an aqueous diL-lysine monosulfate trihydrate solution. The aqueous diL-lysine sulfate monosulfate trihydrate solution may be as described above. The poor solvent is not limited provided that it reduces the solubility of the diL-lysine monosulfate trihydrate, and, for example, methanol, ethanol or 2-isopropyl alcohol. The amount of the poor solvent which is added should be sufficient to allow diL-lysine monosulfate trihydrate crystals to form, and is usually 5 to 30 vol %. The temperature is usually −10 to 35° C.

Following the crystallization step, the diL-lysine monosulfate trihydrate crystals are separated from the mother liquor by usual methods of separation, including but not limited to, suction filtration, centrifugal filtration, centrifugal separation, and press filtration. Following separation, the crystals can be dried by any of the usual methods known in the art and collected for use in industry.

Transition Crystallization

Transition of plate crystals of diL-lysine monosulfate trihydrate to column crystals may be conducted by preparing a slurry of diL-lysine monosulfate plate crystals at a temperature above approximately 40° C., lowering the temperature until it is between approximately −10 to 35° C., allowing crystals to form, and recovering said crystals.

The slurry of plate crystals may be prepared by adding an amount of diL-lysine sulfate which exceeds the solubility of diL-lysine sulfate in water, and stirring and aging overnight at a temperature above approximately 40° C. The pH of slurry is not limited provided that the state of slurry is maintained, and usually 5.0 to 7.0.

Water Solubility of diL-Lysine Mono sulfate Trihydrate

Figure 4:
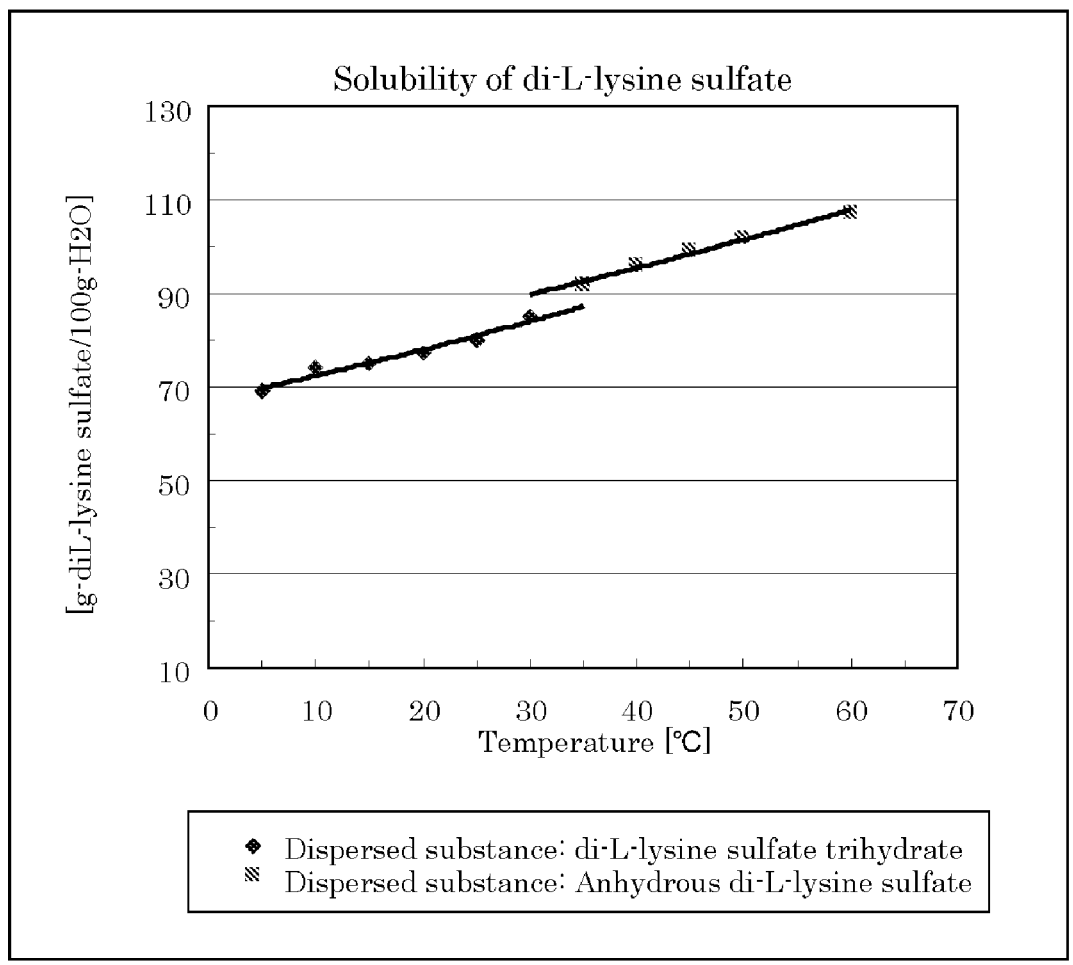
FIG. 4 is a graph showing the relationship between temperature and solubility of diL-lysine sulfate.

DiL-lysine monosulfate trihydrate precipitates at 35° C. and below, and anhydrous diL-lysine sulfate precipitates at 40° C. and above. Normally, solubility in water tends to continuously drop as the temperature decreases. However, as shown in FIG. 4, the solubility curve of diL-lysine monosulfate trihydrate was surprisingly discontinuous with that of anhydrous diL-lysine sulfate. That is, over the temperature range at which diL-lysine monosulfate trihydrate precipitated, the degree of solubility was lower than the degree of solubility that would be expected from the solubility curve of anhydrous diL-lysine sulfate. Thus, crystals precipitating as diL-lysine monosulfate trihydrate were found to have a better crystallization yield than crystals precipitating as anhydrous diL-lysine sulfate. This is because for the diL-lysine monosulfate trihydrate crystals, the water itself is captured in the crystal lattice so that when crystallization proceeds, the available free water in the supernatant decreases. Therefore, there is less supernatant water to aid in dissolution of lysine sulfate. This contributes to the higher yield, that is, more crystal precipitates.

Characteristics of diL-Lysine Monosulfate Trihydrate

Figure 5:
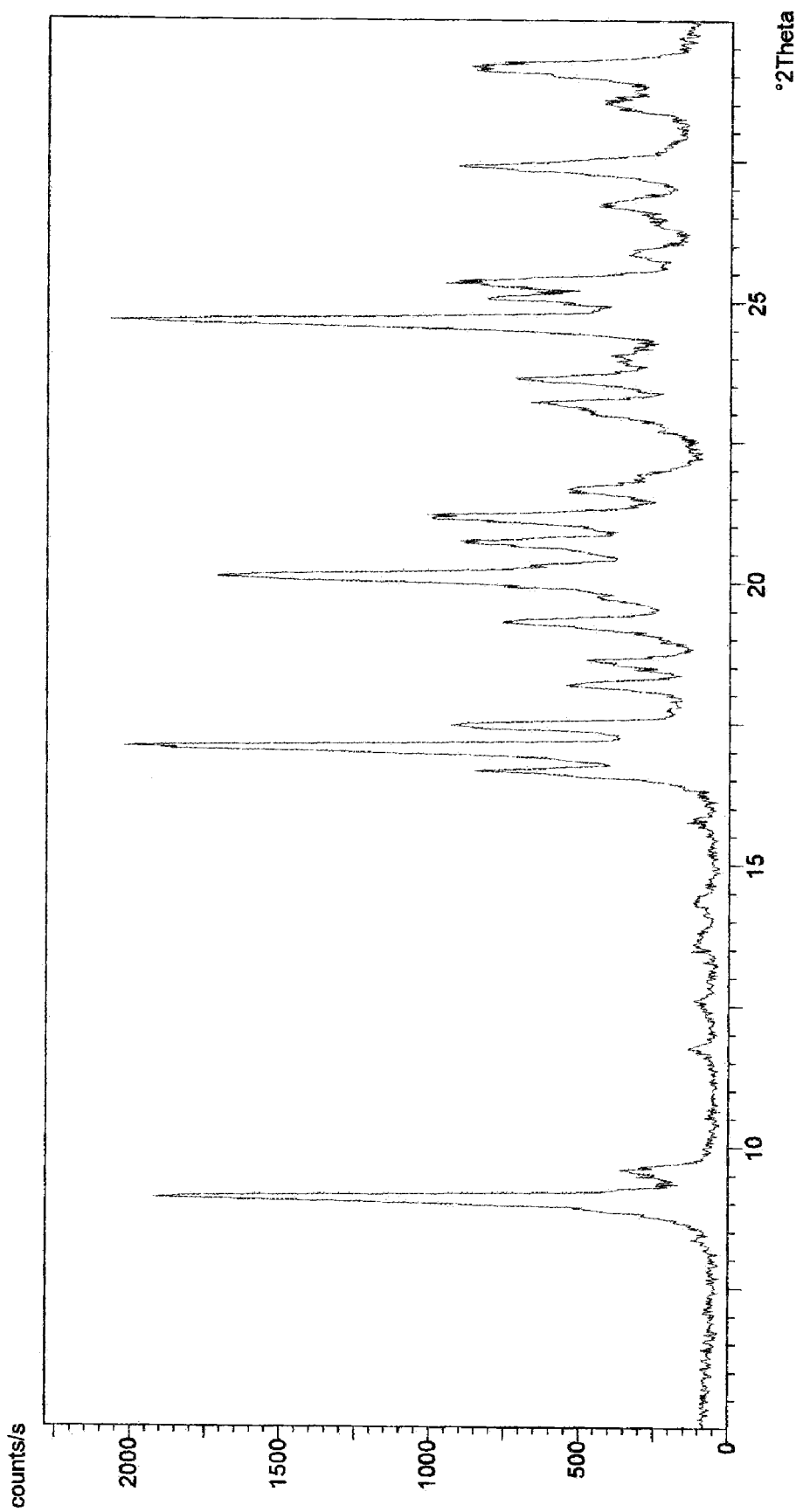
FIG. 5 shows the powder X-ray diffraction pattern of diL-lysine monosulfate trihydrate crystals.

Powder X-ray diffraction, thermal analysis, and L-lysine content analysis were conducted to further elucidate the characteristics of the diL-lysine monosulfate trihydrate crystals of the present invention. FIG. 5 shows the powder X-ray diffraction of diL-lysine monosulfate trihydrate crystals and FIG. 6 shows the powder X-ray diffraction of diL-lysine mono sulfate trihydrate crystals.

Figure 6:
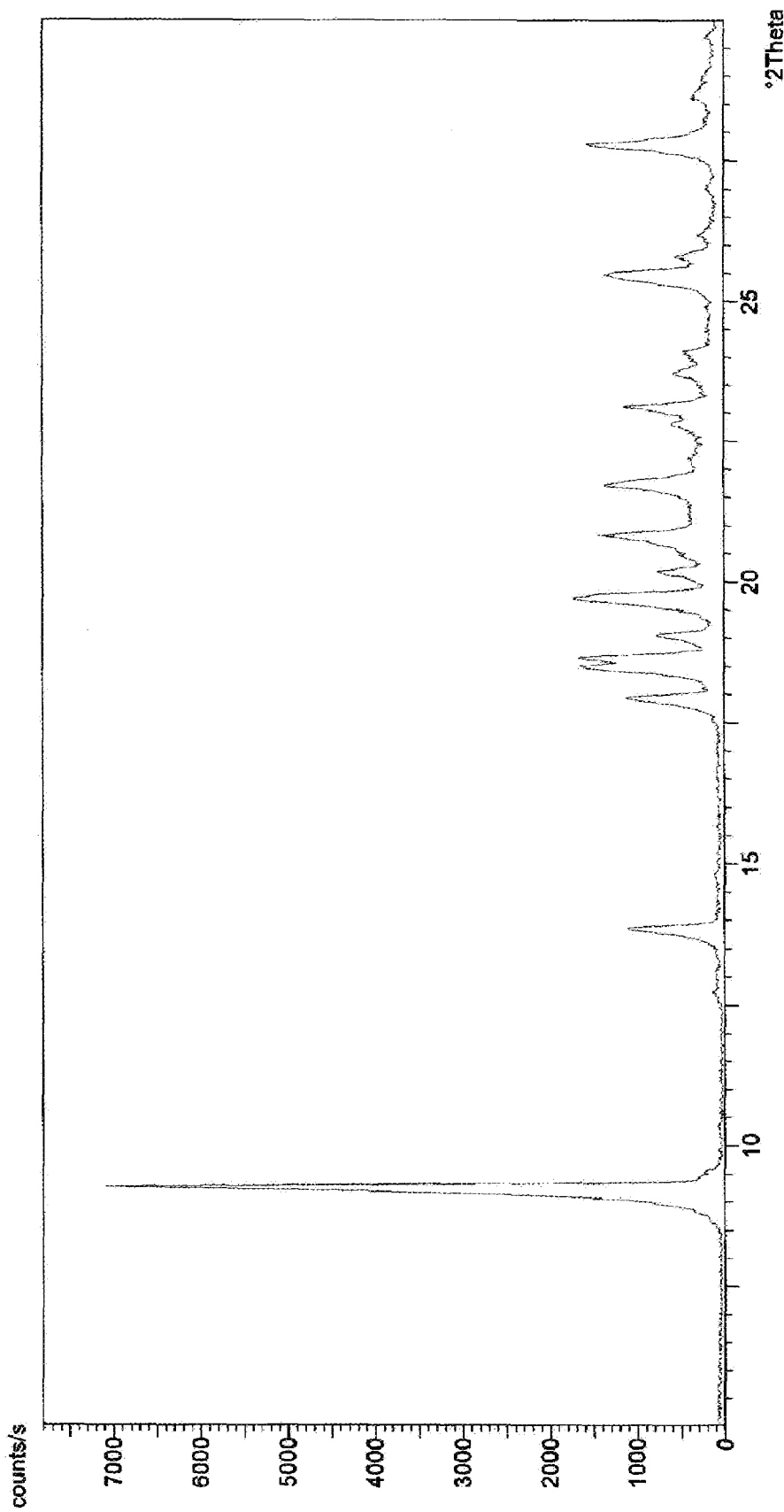
FIG. 6 shows the powder X-ray diffraction pattern of anhydrous diL-lysine sulfate crystals.

As shown in FIGS. 5 and 6, diL-lysine monosulfate trihydrate crystals exhibited diffraction peaks when the diffraction angle $2\theta=16.6°$ and $17.0°$. These diffraction peaks were not exhibited by the anhydrous diL-lysine sulfate crystals. Additionally, although anhydrous diL-lysine sulfate exhibited a diffraction peak at a diffraction angle of $2\theta=13.8°$, this diffraction peak was not exhibited by diL-lysine monosulfate trihydrate crystals. Since diL-lysine monosulfate trihydrate crystals and anhydrous diL-lysine sulfate crystals exhibit different powder X-ray diffraction patterns, the two were determined to have different crystalline forms.

Figure 7:
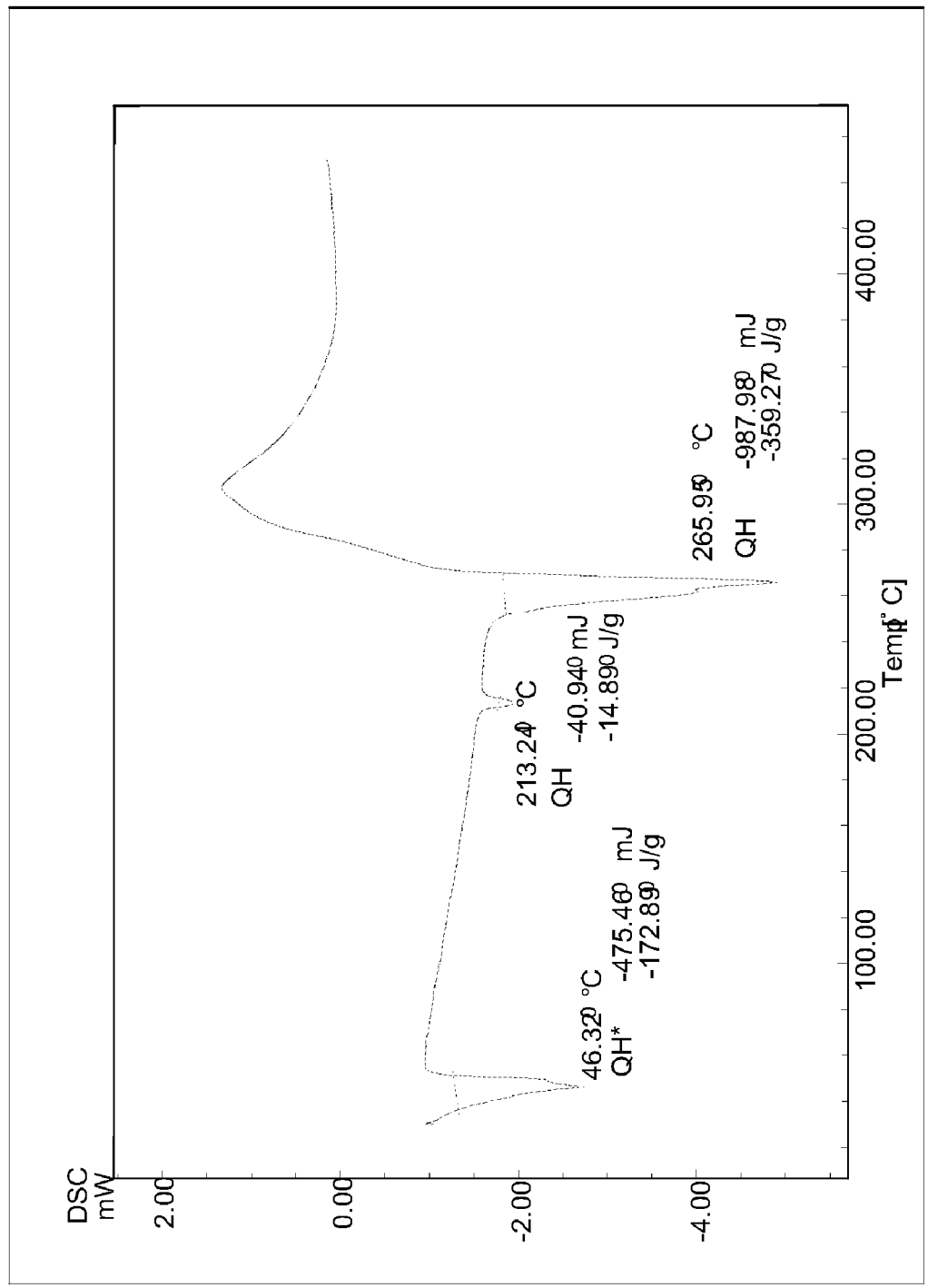
FIG. 7 shows the thermal analysis results for diL-lysine monosulfate trihydrate crystals.
Figure 8:
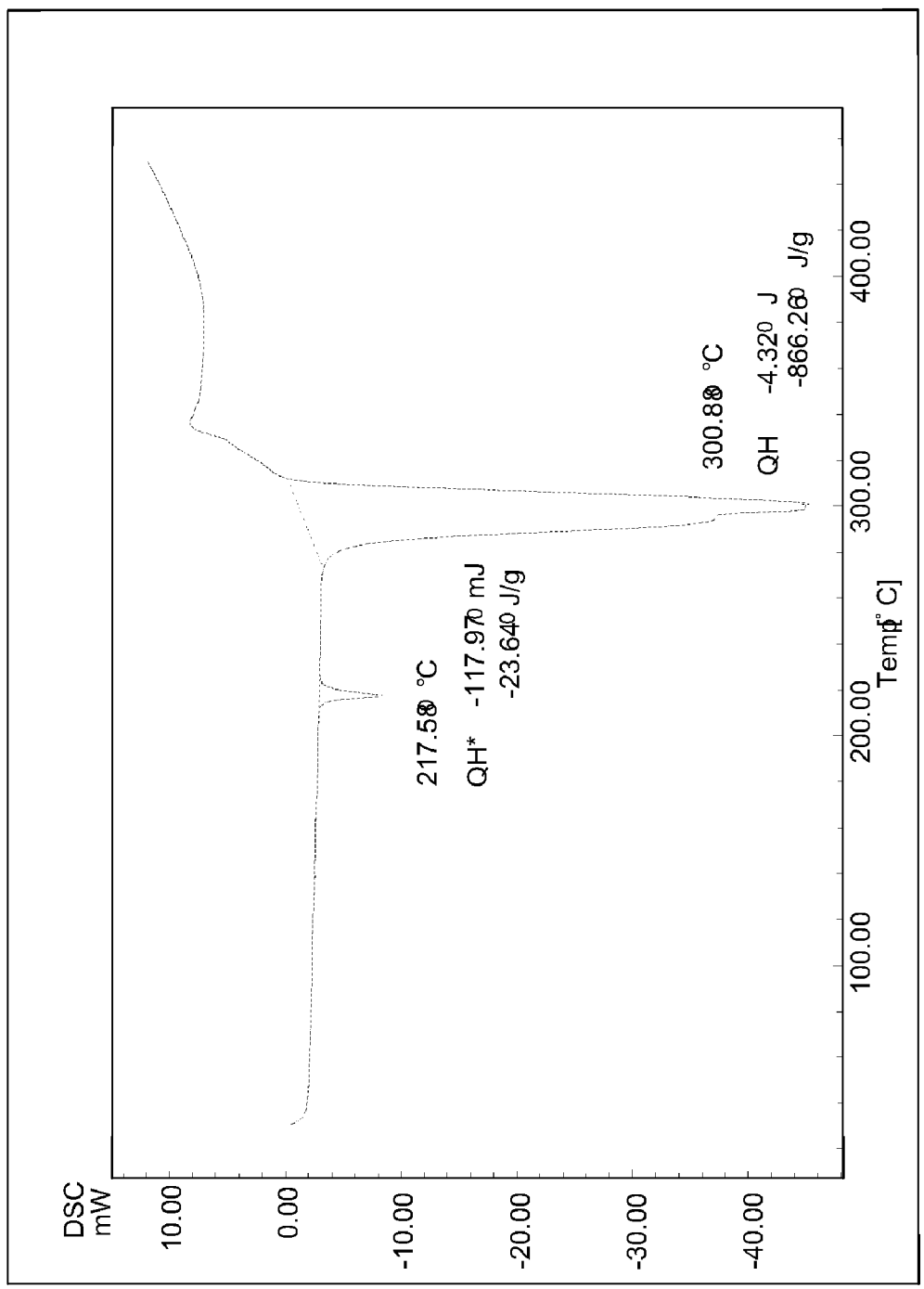
FIG. 8 shows the thermal analysis results for anhydrous diL-lysine sulfate.

Thermal analysis was conducted to further elucidate the properties of diL-lysine monosulfate trihydrate crystals. FIG. 7 shows the thermal analysis results for diL-lysine monosulfate trihydrate crystals and FIG. 8 shows the thermal analysis results for anhydrous diL-lysine sulfate crystals. Comparing FIGS. 7 and 8, the two crystals both exhibited heat absorption peaks in the vicinity of 215° C. and 300° C. This was attributed to melting of diL-lysine sulfate or heat absorption accompanying decomposition.

A heat absorption peak was uniquely observed in diL-lysine monosulfate trihydrate at 45 to 60° C. This was presumed to be the heat absorption peak occurring as diL-lysine monosulfate trihydrate crystals lost their water. Since diL-lysine monosulfate trihydrate loses its water at an extremely low temperature in this manner, diL-lysine monosulfate trihydrate crystals readily lose their crystal water during the drying step, which is extremely advantageous to the industrial production of anhydrous diL-lysine sulfate. Usually, the crystal may be dried at not less than 40° C. overnight, to remove the crystal water. If the temperature is less than 40° C., the crystals may remain as a hydrate. The upper limit of the drying temperature is not limited unless the crystals decompose, and is usually determined from the viewpoint of costs.

The L-lysine content of the diL-lysine monosulfate trihydrate crystals obtained by the method of example 1 is preferably around 65%. L-lysine can be measured by any method known to those in the art, including HPLC. More preferably, the L-lysine content can be increased to greater than 75% by converting the crystals to an anhydrous state by eliminating the crystal water at approximately 46° C. Japanese Unexamined Patent Publication (KOKAI) Heisei No. 5-192089 provides examples of substances commonly containing diL-lysine sulfate obtained by directly drying the fermentation broth, and therefore, employing no purification step. Crystals obtained by this method typically contain below 50% L-lysine. Therefore, by comparison, the crystals of the present invention are superior in that they contain a higher L-lysine content.

The present invention will be more concretely explained below with reference to following Examples, which are intended to be illustrative only and are not intended to limit the scope of the invention as defined by the appended claims.

EXAMPLES

The data disclosed herein were obtained by analysis under the following conditions:
  a. L-lysine content: Hitachi Amino Acid Analyzer L-8800 (protein hydrolysis product analysis method)
  b. Powder X-ray diffraction: Phillips X'Pert TYPE PW3040/00 (X-ray: CuKα, wave length: 1.5418 Å)
  c. Thermal analysis: Shimadsu Seisakujo differential Scanning Calorimeter DSC-60
  d. Elemental Analysis: Analysis of carbon, hydrogen, and nitrogen was by elemental analyzer vario EL3 (elemental); analysis of oxygen was by organic element analyzer CHN-O-Rapid (elemental); analysis of sulfer was by Ion chlomato analyzer (sulfer was analyzed as sulfuric acid, which is generated by combustion with oxygen); all analyses conducted by Tore Research Center Example 1

A 584 g quantity of 50% L-lysine solution obtained from a commercial source (Daiichi Fine Chemicals, Ltd., lot A2882) was placed in a 500 ml glass beaker and maintained at 10° C. in a water bath. A 102 g quantity of 98% sulfuric acid (reagent grade, Junsei Kagaku lot 1L8102) was then added and the L-lysine was converted to diL-lysine sulfate. As a result, large columnar crystals precipitated, as shown in FIG. 1.

The slurry obtained was stirred and aged overnight at 5° C., after which the mother liquid and crystals were separated by suction filtration using filter paper.

Figure 9:
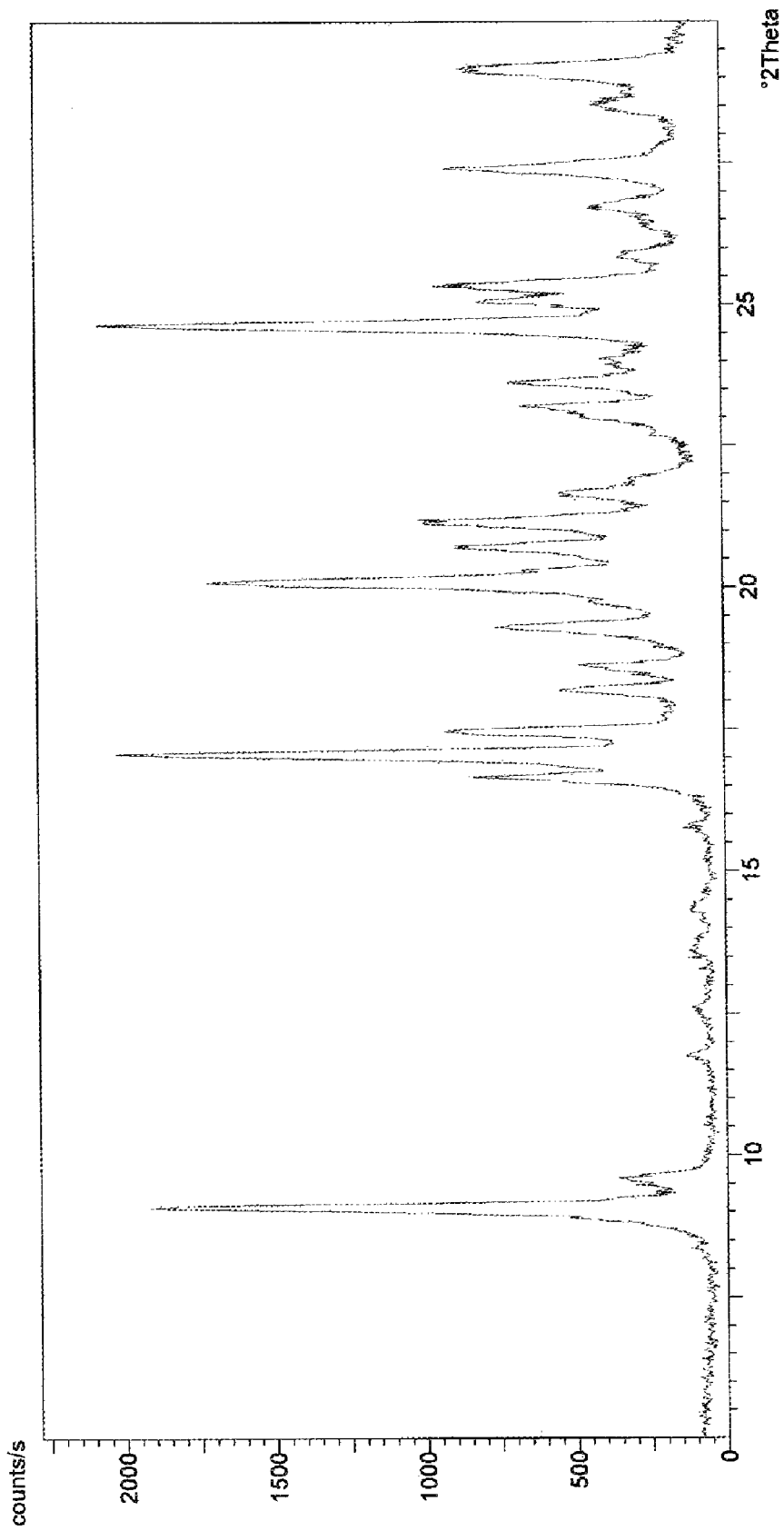
FIG. 9 shows the powder X-ray diffraction pattern of crystals obtained in Example 1.

Table 1 shows the results of elemental analysis. FIG. 9 shows the powder X-ray diffraction chart.

TABLE 1

|  | Example 1 | Theoretical values of diL-lysine monosulfate trihydrate crystal $2(C_6H_{16}N_2O_2) \cdot SO_4 \cdot 3H_2O$ |
|---|---|---|
| Carbon | 32.38% | 32.3% |
| Hydrogen | 8.16% | 8.5 |
| Nitrogen | 12.42% | 12.6 |
| Oxygen | 38.25% | 39.5 |
| Sulfur | 7.34% | 7.2 |

FIG. 7 shows the thermal analysis results. The analysis conditions are as follows:

TABLE 2

*) QH means Quantity of Heat

| File name: | 2002-10-17 09-51.tad |
|---|---|
| Unit designation: | DSC60 |
| Collection date: | 02/10/17 |
| Collection time: | 09:51:54 |
| Sample designation: | 2-lysine sulfate 3 hydrate [Al slow] |
| Sample quantity: | 2.750 [mg] |
| Comments: | ref empty |

[Temperature Program]

Starting temperature: 30.0

| Heating rate [° C./min] | Hold temp. [° C.] | Hold time [min] | Gas |
|---|---|---|---|
| 2.00 | 450.0 | 0 | Nitrogen |

As shown in Table 1, the elemental analysis results of the crystals obtained in Example 1 approximated the theoretical elemental composition of diL-lysine monosulfate trihydrate. Accordingly, the crystals obtained in Example 1 were determined to be diL-lysine monosulfate trihydrate.

As shown in FIG. 9, the crystals obtained in Example 1 exhibited diffraction peaks at diffraction angles 2θ=16.6° and 17.0°, and did not exhibit a diffraction peak at 13.6°. Thus, they were determined to be diL-lysine monosulfate trihydrate.

Example 2

For comparison purposes, diL-lysine sulfate crystallization was conducted by the same method as in Example 1 with the exception that the crystallization temperature was 45° C. A powder X-ray pattern was immediately obtained for the crystals obtained by separation from the mother liquor. The separated crystals were also dried at 105° C. and subjected to elemental analysis.

Figure 10:
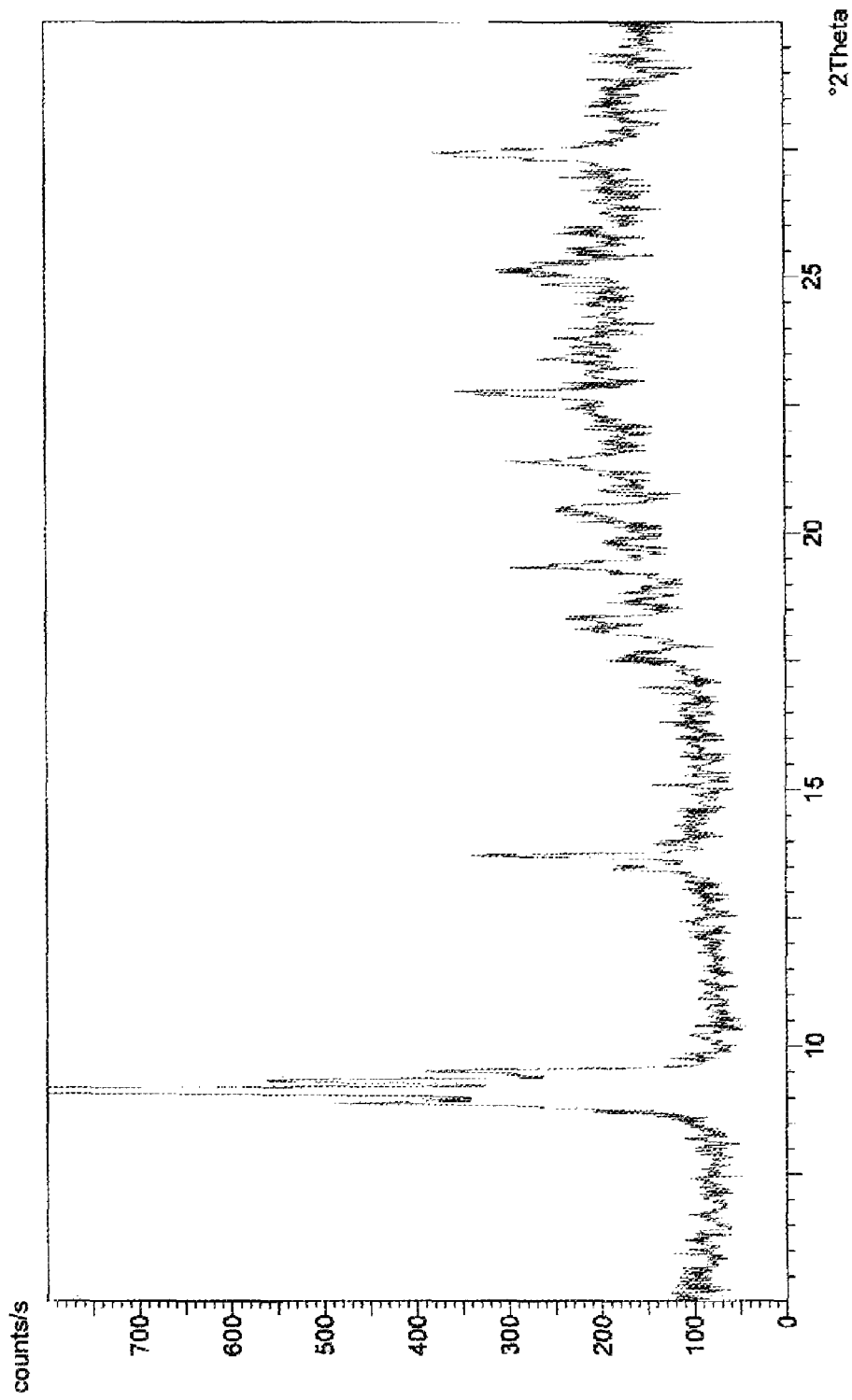
FIG. 10 shows the powder X-ray diffraction pattern of crystals obtained in Example 2.
Figure 11:
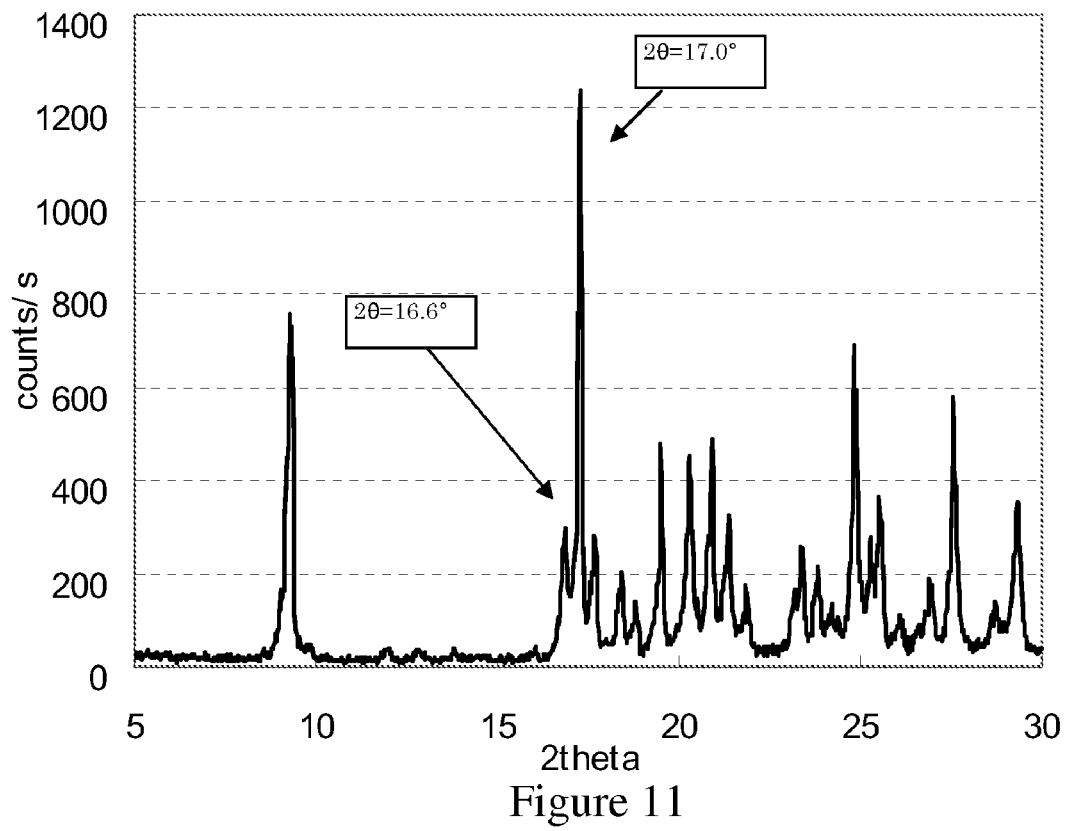
FIG. 11 shows the powder X-ray diffraction pattern of crystals obtained in Example 3 (crystallization by concentration).
Figure 12:
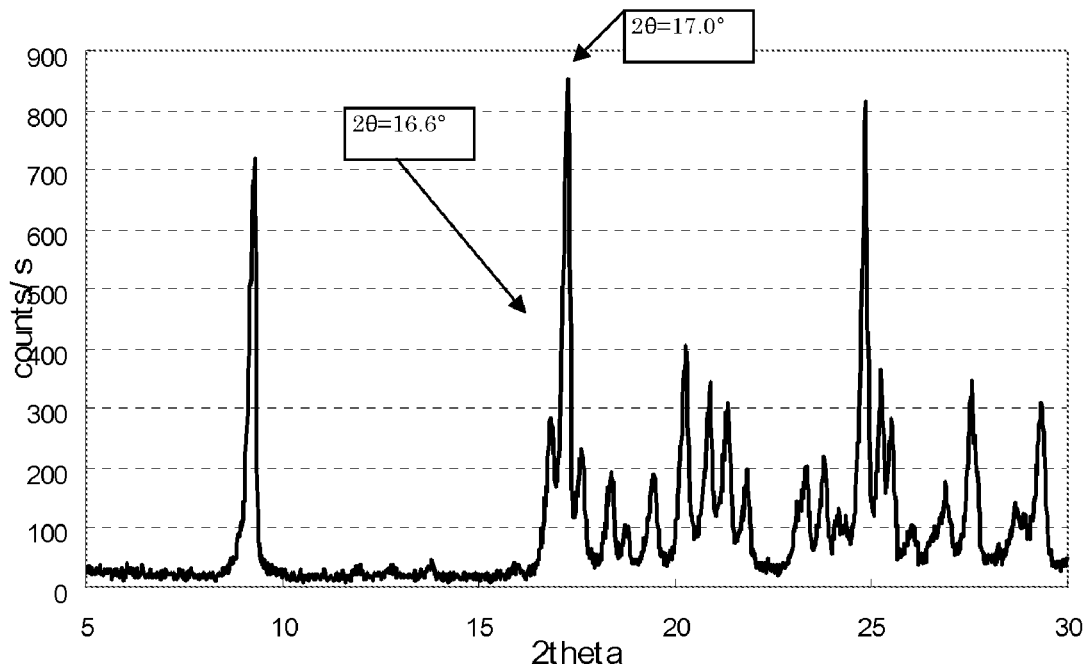
FIG. 12 shows the powder X-ray diffraction pattern of crystals obtained in Example 3 (crystallization by cooling).
Figure 13:
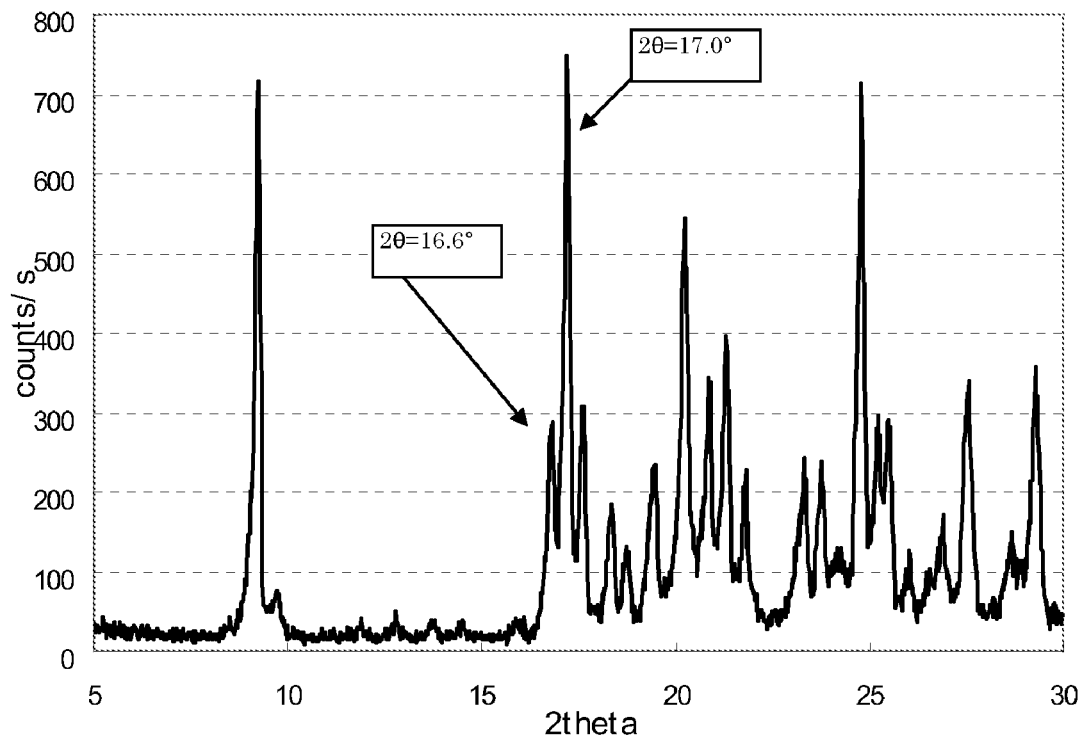
FIG. 13 shows the powder X-ray diffraction pattern of crystals obtained in Example 3 (crystallization by rearrangement).
Figure 14:
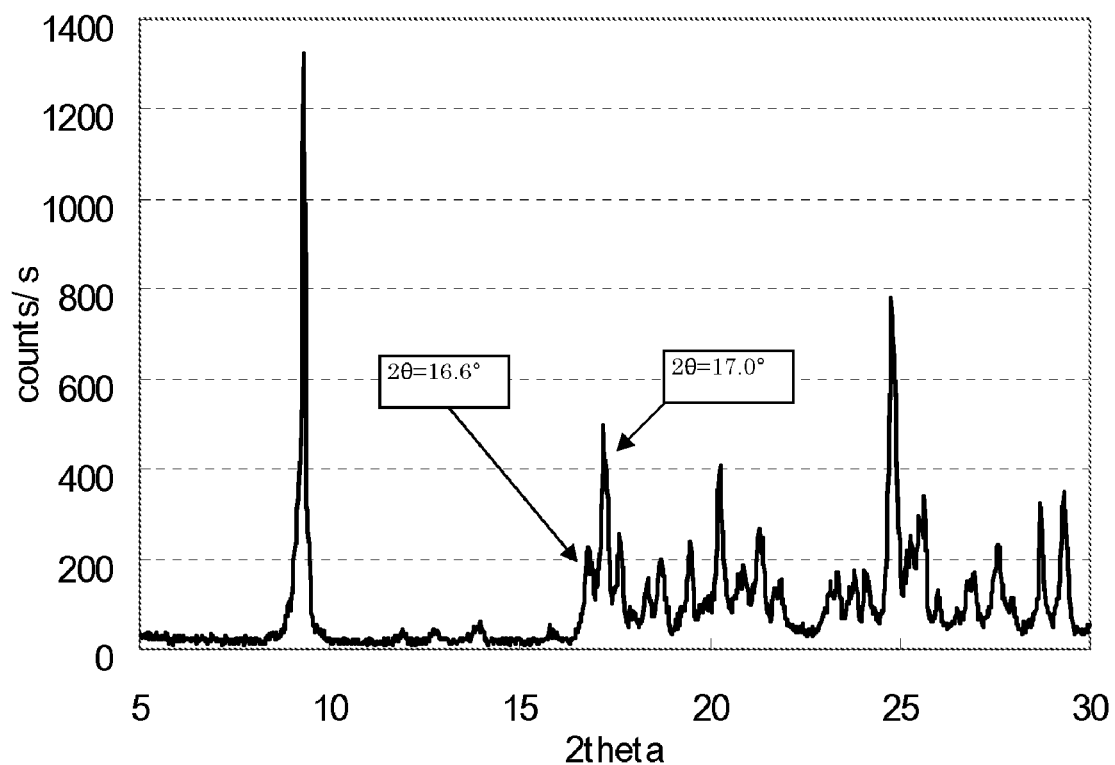
FIG. 14 shows the powder X-ray diffraction pattern of crystals obtained in Example 3 (crystallization by methanol addition).
Figure 15:
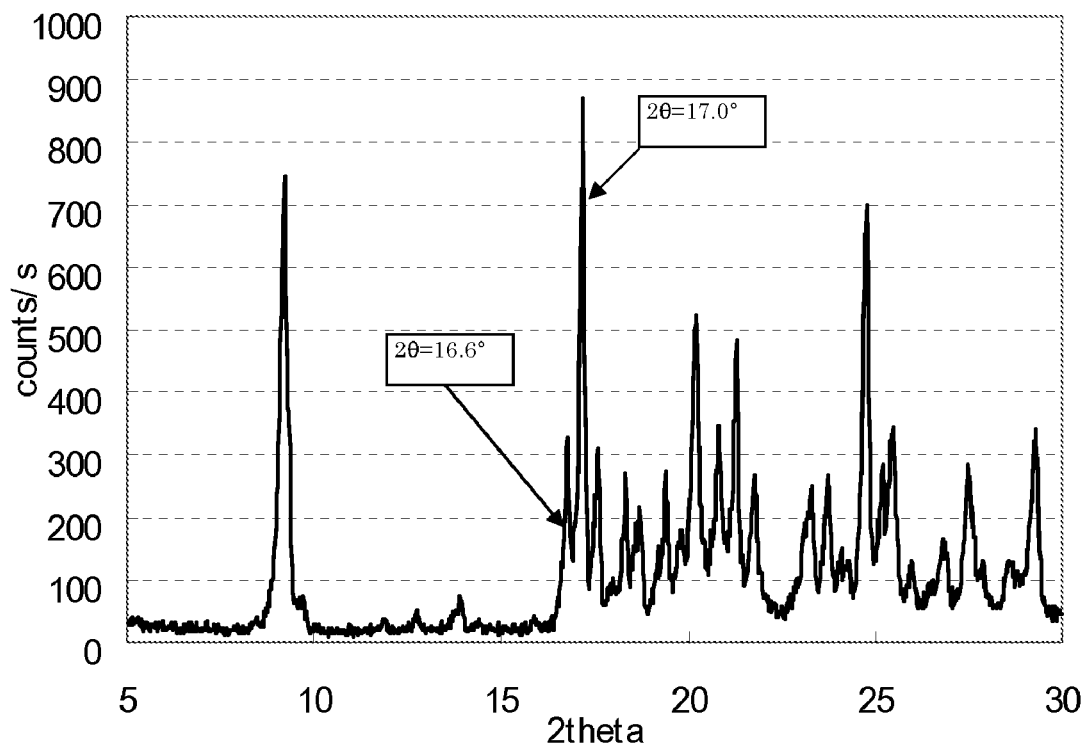
FIG. 15 shows the powder X-ray diffraction pattern of crystals obtained in Example 3 (crystallization by ethanol addition).
Figure 16:
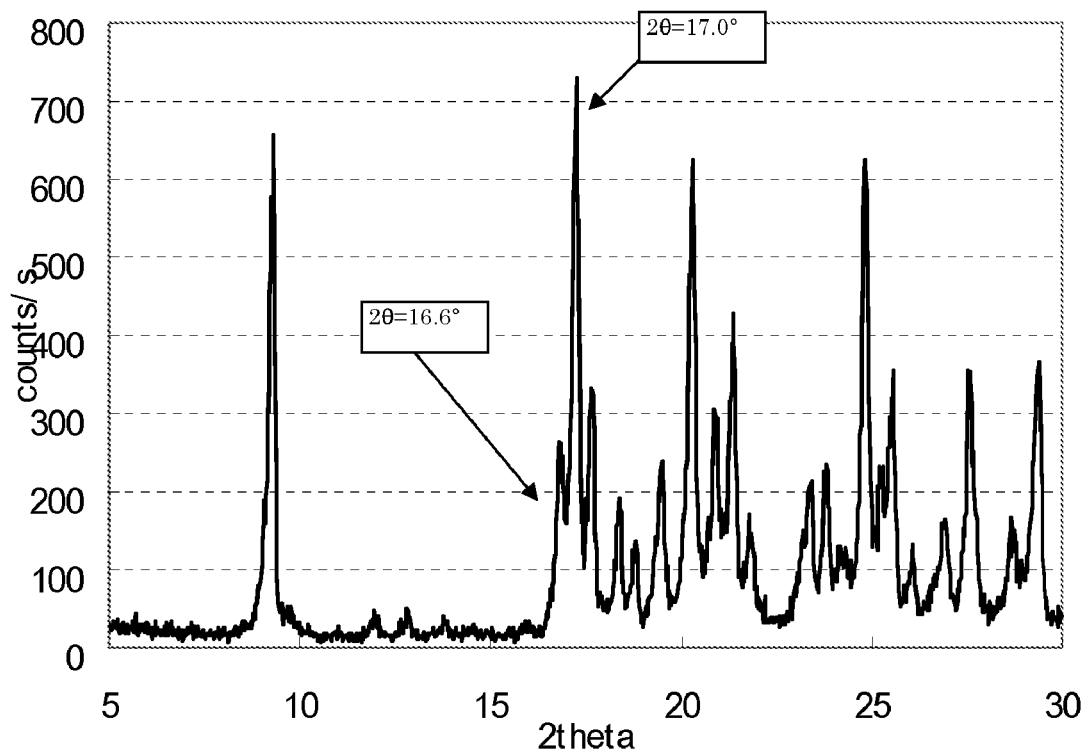
FIG. 16 shows the powder X-ray diffraction pattern of crystals obtained in Example 3 (crystallization by 2-isopropyl alcohol addition).

FIG. 10 shows the powder X-ray pattern. Table 3 shows the results of elemental analysis.

TABLE 3

|  | Example 2 | Theoretical values of anhydrous diL-lysine sulfate crystal $2(C_6H_{16}N_2O_2) \cdot SO_4$ |
|---|---|---|
| Carbon | 36.76% | 36.7% |
| Hydrogen | 7.75% | 8.2 |

TABLE 3-continued

| | Example 2 | Theoretical values of anhydrous diL-lysine sulfate crystal $2(C_6H_{16}N_2O_2) \cdot SO_4$ |
|---|---|---|
| Nitrogen | 14.12% | 14.3% |
| Oxygen | 31.91% | 32.7% |
| Sulfur | 8.32% | 8.2% |

FIG. 8 shows the thermal analysis results. The analysis conditions are as follows:

TABLE 4

*) QH means Quantity of Heat

| File name: | 2002-10-16 11-33.tad |
|---|---|
| Unit designation: | DSC60 |
| Collection date: | 02/10/16 |
| Collection time: | 11:33:50 |
| Sample designation: | 2-lysine sulfate [Al] |
| Sample quantity: | 4.990 [mg] |
| Comments: | ref empty |

[Temperature Program]

Starting temperature: 30.0

| Heating rate [° C./min] | Hold temp. [° C.] | Hold time [min] | Gas |
|---|---|---|---|
| 10.00 | 450.0 | 0 | Nitrogen |

As shown in Table 3, the analytic values of the crystals obtained in Example 2 approximated the theoretical values of anhydrous diL-lysine sulfate crystals. Accordingly, the crystals obtained in Example 2 were determined to be anhydrous diL-lysine sulfate.

As shown in FIG. 10, the anhydrous diL-lysine sulfate crystals exhibited a unique diffraction peak at a diffraction angle of $2\theta=13.8°$. Further, the $2\theta=16.6°$ and $17.0°$ peaks unique to diL-lysine monosulfate trihydrate crystals were not observed. Accordingly, the crystals obtained in Example 2 were determined to be anhydrous diL-lysine sulfate.

Example 3

1. Concentration Crystallization

A 320 g quantity of an aqueous diL-lysine sulfate solution which had a L-lysine concentration of 34.5 wt % and a pH which was adjusted to 7, was used as a starting material and concentrated to about 1.5 fold by using a rotary evaporator (pressure: 30 mmHg, water bath temperature: 40° C.). As a result, precipitation of column crystals was observed.

2. Cooling Crystallization

A diL-lysine sulfate slurry, the pH of which was adjusted to 7, was stirred and aged overnight at 60° C. Then, the saturated diL-lysine sulfate solution and crystals were separated by suction filtration using filter paper. The saturated diL-lysine sulfate solution was used as a starting material and cooled from 60° C. to 10° C. As a result, precipitation of column crystals was observed.

3. Solvent Addition Crystallization

A 320 g quantity of an aqueous diL-lysine sulfate solution which had a L-lysine concentration of 34.5 wt % and pH of which was adjusted to 7, was used as a starting material and methanol, ethanol, and 2-propyl alcohol were each added to the solution in an amount of 20% (v/v) each. As a result, precipitation of column crystals was observed.

4. Transition Crystallization

A diL-lysine sulfate slurry, the pH of which was adjusted to 7, was stirred and aged overnight at 60° C. to obtain a slurry containing only small plate crystals (anhydrous diL-lysine sulfate crystals). Then, the slurry was cooled from 60° C. to 10° C. As a result, all plate crystals were converted to column crystals.

With respect to each of the products obtained in above 1 to 4, the mother liquid and crystals were separated by suction filtration using filter paper. The obtained crystals were dried at room temperature, the L-lysine content determined, and power X-ray diffraction, thermal analysis, and elemental analysis were conducted.

The data disclosed in this example were obtained by analysis under the following conditions:

L-lysine content: Hitachi Amino Acid Analyzer L-8800 (protein hydrolysis product analysis method)

Powder X-ray diffraction: Phillips X'Pert TYPE PW3040/00 (X-ray: CuKα, wave length: 1.5418 Å)

Thermal analysis: SEIKO INSTRUMENTS differential Scanning Calorimeter TG/TDA220 SII Elemental Analysis: all analyses conducted by Tore Research Center (Report No. P101976-01)

All of the crystals obtained by the various crystallization methods in this Example were thick column crystals and were different from the crystal form of anhydrous diL-lysine sulfate.

The L-lysine content of crystals obtained by each of the crystallization methods is shown in Table 5.

TABLE 5

| | Crystallization method | | | | | [Unit: wt %] |
|---|---|---|---|---|---|---|
| | Centration | Cooling | Transition | Solvent addition (methanol) | Solvent addition (ethanol) | Solvent addition (2-isopropyl alcohol) |
| L-lysine content | 66 | 68 | 66 | 66 | 65 | 66 |

(Theoretical L-lysine content of diL-lysine monosulfate trihydrate: 66 wt %, theoretical L-lysine content of anhydrous diL-lysine sulfate: 75 wt %)

As shown in Table 5, the L-lysine content of the crystals obtained in this Example was approximately 66 wt % and agreed with the theoretical L-lysine content of diL-lysine monosulfate trihydrate, 65 wt %. FIGS. 11 to 16 show the power X-ray diffraction patterns of crystals obtained by each of the crystallization methods. As shown in FIGS. 11 to 16, the crystals obtained by each of the crystallization methods in this Example exhibited unique diffraction peaks at diffraction angles $2\theta=16.6°$ and $17.0°$. Thus, they were all determined to be diL-lysine monosulfate trihydrate crystals.

In the thermal analysis conducted with respect to the crystals obtained in this Example, a heat adsorption peak was uniquely observed at 50 to 60° C. This was presumed to be the heat absorption peak occurring as diL-lysine monosulfate trihydrate crystals lost their water.

Table 6 shows the results of elemental analysis of the crystals obtained by each of the crystallization methods.

TABLE 6

| | Theoretical values of diL-lysine monosulfate trihydrate cyrstal $2(C_6H_{16}N_2O_2)\cdot SO_4\cdot 3H_2O$ | Concentration crystallization | Cooling crystallization | Transition crystallization | Solvent addition Methanol | Solvent addition Ethanol | Solvent addition 2-Isopropyl alcohol |
|---|---|---|---|---|---|---|---|
| Carbon | 32.3% | 31.97% | 31.75% | 31.86% | 32.48% | 32.63% | 31.87% |
| Hydrogen | 8.5% | 8.24% | 8.22% | 8.25% | 8.14% | 8.13% | 8.19% |
| Nitrogen | 12.6% | 12.45% | 12.34% | 12.39% | 12.60% | 12.69% | 12.38% |
| Oxygen | 39.5% | 39.17% | 39.80% | 39.14% | 37.57% | 37.30% | 38.80% |
| Sulfer | 7.2% | 7.26% | 7.11% | 7.10% | 7.41% | 7.37% | 7.15% |

As shown in Table 6, the elemental analysis results of the crystals obtained in this Example approximated the theoretical elemental composition of diL-lysine monosulfate trihydrate. Accordingly, all of the crystals obtained in this Example were determined to be diL-lysine monosulfate trihydrate.

Example 4

*Brevibacterium flavum* AJ 11275 (NRRL B-11474) was inoculated into a medium (pH 7.2) containing glucose 100 g/L, ammonium sulfate 8.0 g/L, Yeast Extract (Basco) 1.05 g/L, $KH_2PO_4$ 1.0 g/L, $MgSO_4\cdot 7H_2O$ 0.4 g/L, $FeSO_4\cdot 7H_2O$ 10 mg/L, $MnSO_4\cdot 4H_2O$ 10 mg/L, vitamin B, hydrochloride 0.2 mg/L, biotin 0.05 mg/L, and Surfactant GD-113 (Nippon Jushi) 0.05 mg/L, and culture with stirring at 31.5° C. for 70 hours to obtain L-lysine fermentation broth. The L-lysine content of the obtained broth was 3.46 wt %.

The broth was centrifuged at 4500 rpm, 25° C. for 20 minutes by using a refrigerated high speed centrifuge (KUBOTA model 7930), and the supernatant was used as a cell-removed solution. The cell-removed solution was used as a starting material and concentrated to about 4 fold by using a rotary evaporator (pressure: 30 mmHg, water bath temperature: 60° C.), and then the conditions were changed (pressure: 20 mmHg, water bath temperature: 40° C.) to concentrate to about 10 folds in total. As a result, precipitation of column crystals was observed.

The obtained slurry was stirred and aged at 10° C. for about 40 hours, after which the mother liquid and crystals were separated by swing separation using filter cloth.

The obtained crystals were dried at room temperature, and washed 5 times by a saturated L-lysine solution and then washed by ethanol. The obtained crystals were thick column crystals and were different from the crystal form of anhydrous diL-lysine sulfate. The L-lysine content of the obtained crystals was 63 wt % (Theoretical content: 65 wt %). Hereinafter, the crystals are called "Crystals I".

Figure 17:
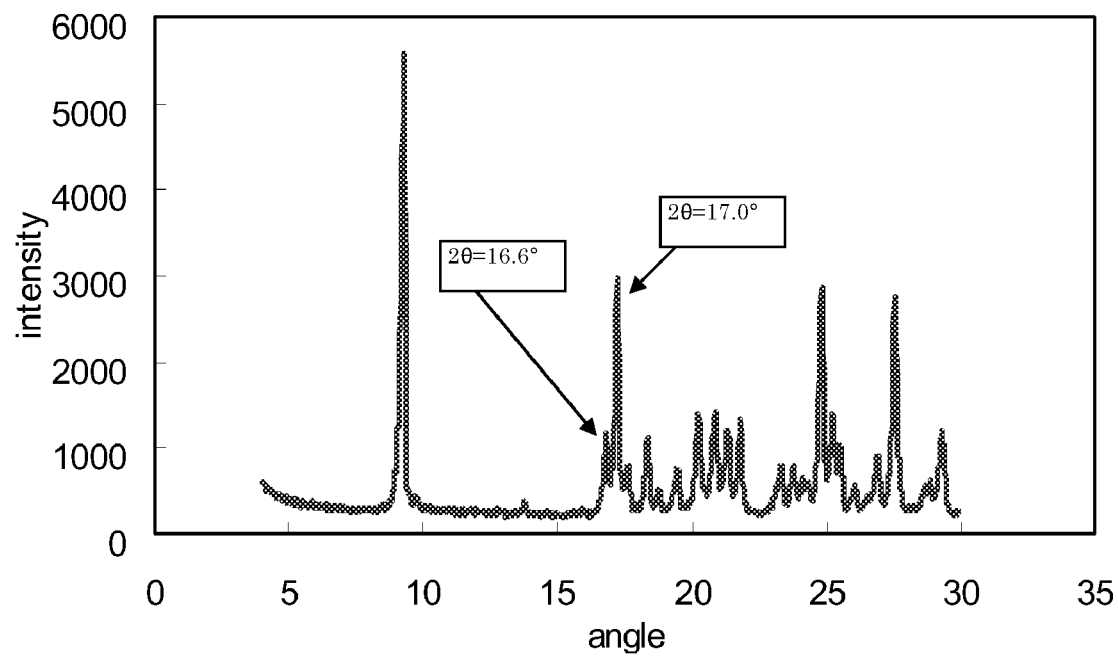
FIG. 17 shows the powder X-ray diffraction pattern of crystals obtained in Example 4 (crystals I).

FIG. 17 shows the powder X-ray pattern of Crystals I (diL-lysine monosulfate trihydrate).

As shown in FIG. 17, the Crystals I (dried at room temperature, 25° C.) obtained in this Example exhibited diffraction peaks at diffraction angles 2θ=16.6° and 17.0°, which are unique to diL-lysine monosulfate trihydrate. Thus, they were determined to be diL-lysine monosulfate trihydrate.

Table 7 shows the results of elemental analysis of the crystals obtained by the crystallization method.

TABLE 7

| | C (%) | H (%) | N (%) | O (%) | S (%) |
|---|---|---|---|---|---|
| Theoretical value of diL-lysine monosulfate trihydrate crystal | 32.3 | 8.5 | 12.6 | 39.5 | 7.2 |
| Crystals I obtained in Example 4 | 32.0 | 8.3 | 12.4 | 39.9 | 6.8 |

As shown in Table 7, the elemental analysis results of the Crystals I obtained in this Example approximated the theoretical elemental composition of diL-lysine monosulfate trihydrate. Accordingly, the Crystals I was determined to be diL-lysine mono sulfate trihydrate.

Then, the obtained diL-lysine monosulfate trihydrate crystals were dried at 105° C. for 36 hours to obtain anhydrous diL-lysine sulfate. The L-lysine content of the obtained anhydrous diL-lysine sulfate was 74 wt % (theoretical contet: 74 wt %). Hereinafter, the crystals were called as Crystals II.

Figure 18:
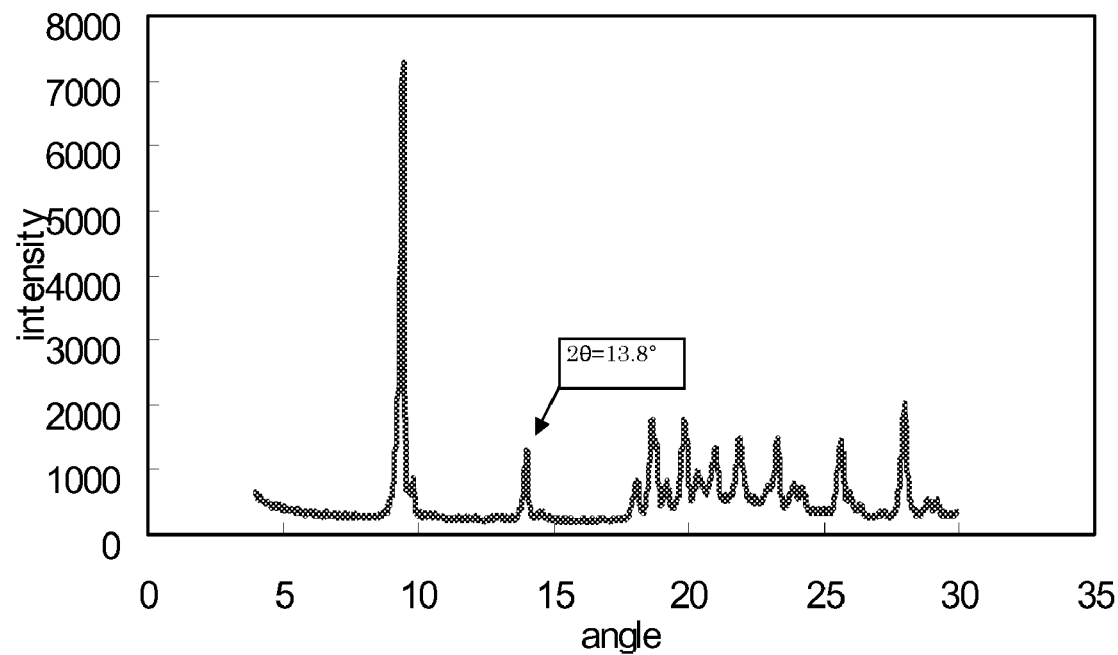
FIG. 18 shows the powder X-ray diffraction pattern of crystals obtained in Example 4 (crystals II).

FIG. 18 shows the powder X-ray pattern of Crystals II obtained by drying at 105° C. (anhydrous diL-lysine sulfate).

As shown in FIG. 18, the Crystals II obtained by by drying at 105° C. in this Example exhibited a diffraction peak at a diffraction angle of 2θ=13.8° unique to anhydrous diL-lysine sulfate. Accordingly, the crystals were determined to be anhydrous diL-lysine sulfate.

Table 8 shows the results of elemental analysis.

TABLE 8

| | C (%) | H (%) | N (%) | O (%) | S (%) |
|---|---|---|---|---|---|
| Theoretical value of diL-lysine monosulfate trihydrate crystal | 36.7 | 8.2 | 14.3 | 32.7 | 8.2 |
| Crystals II obtained in Example 4 | 36.9 | 7.8 | 14.3 | 32.6 | 8.2 |

As shown in Table 8, the analytic values of the crystals II obtained in this Example approximated the theoretical values of anhydrous diL-lysine sulfate crystals. Accordingly, the crystals were determined to be anhydrous diL-lysine sulfate obtained through diL-lysine mono sulfate trihydrate.

The L-lysine content determination, the power X-ray analysis, and the elemental analysis were the same as those of Example 3.

In view of the above results, it has been found that anhydrous diL-lysine sulfate can be obtained from an actual fermentation broth though diL-lysine monosulfate trihydrate.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

INDUSTRIAL APPLICABILITY

A diL-lysine monosulfate trihydrate crystal is described which has a large tabular form and is more easily separable from the mother liquor.

The invention claimed is:

1. A method of producing a diL-lysine monosulfate trihydrate crystal characterized by having peaks at diffraction angles 2θ of 16.6° and 17.0° as measured by powder X-ray diffraction comprising
    a) mixing a lysine solution with sulfuric acid at a temperature of between approximately −10° and approximately 35° C., and allowing said crystal to form, and
    b) recovering said crystal.

2. The method of claim 1, wherein said temperature is between approximately 0° C. and approximately 20° C.

3. The method of claim 2, wherein said temperature is approximately 10° C.

4. The method of claim 1, wherein said crystal is recovered by filtration.

5. The method of claim 4, wherein said filtration is selected from the group consisting of suction filtration, centrifugal filtration, centrifugal separation, and press filtration.

6. A method of producing diL-lysine sulfate comprising
    a) mixing a lysine solution with sulfuric acid at a temperature of between approximately −10° C. and approximately 35° C., and allowing a crystal to form,
    b) recovering said crystal which is characterized by having peaks at diffraction angles 2θ of 16.6° and 17.0° in powder X-ray diffraction,
    c) drying said crystal to remove the crystal water, and
    d) collecting said diL-lysine sulfate.

7. The method of claim 6, wherein said temperature is between approximately 0° C. and approximately 20° C.

8. The method of claim 7, wherein said temperature is approximately 10° C.

9. The method of claim 6, wherein said crystal is recovered by filtration.

10. The method of claim 9, wherein said filtration is selected from the group consisting of suction filtration, centrifugal filtration, centrifugal separation, and press filtration.

11. A method of producing a diL-lysine inonosulfate trihydrate crystal characterized by having peaks at diffraction angles 2θ of 16.6° and 17.0° in powder X-ray diffraction, comprising
    a) mixing a lysine solution with sulfuric acid at a temperature above approximately 40° C., and allowing crystals to form,
    b) lowering the temperature until it is between approximately −10° C. and approximately 35° C., and allowing crystals to form, and
    e) recovering said diL-lysine mono sulfate trihydrate crystal.

12. The method of claim 11, wherein said temperature in step (b) is between approximately 0° C. and approximately 20° C.

13. The method of claim 12, wherein said temperature in step (b) is approximately 10° C.

14. The method of claim 11, wherein said crystal is recovered by filtration.

15. The method of claim 14, wherein said filtration is selected from the group consisting of suction filtration, centrifugal filtration, centrifugal separation, and press filtration.

16. The method of claim 11, wherein said diL-lysine monosulfate trihydrate crystal is characterized by having peaks at diffraction angles 2θ of 16.6° and 17.0° in powder X-ray diffraction.

17. A method of producing a diL-lysine monosulfate trihydrate crystal characterized by having peaks at diffraction angles 2θ of 16.6° and 17.0° in powder X-ray diffraction, comprising
    a) concentrating an aqueous diL-lysine monosulfate trihydrate solution by evaporation, and allowing a crystal to form, and
    b) recovering said crystal.

18. The method of claim 17, wherein said evaporation occurs under reduced pressure.

19. A method of producing a diL-lysine monosulfate trihydrate crystal characterized by having peaks at diffraction angles 2θ of 16.6° and 17.0° in powder X-ray diffraction, comprising
    a) preparing an aqueous diL-lysine monosulfate trihydrate solution at a temperature above approximately 40° C.,
    b) lowering the temperature until it is between approximately −10° C. and approximately 35° C., and allowing crystals to form, and
    c) recovering said diL-lysine monosulfate trihydrate crystal.

20. The method of claim 19, wherein said solution is saturated.

21. A method of producing a diL-lysine monosulfate trihydrate crystal characterized by having peaks at diffraction angles 2θ of 16.6° and 17.0° in powder X-ray diffraction, comprising
    a) adding a poor solvent to an aqueous diL-lysine mono sulfate trihydrate solution, and allowing a crystal to form, and
    b) recovering said crystal.

22. The method of claim 21, wherein said poor solvent is methanol, ethanol or 2-isopropyl alcohol.

23. A method of producing a diL-lysine monosulfate trihydrate column crystal characterized by having peaks at diffraction angles 2θ of 16.6° and 17.0° in powder X-ray diffraction, comprising
    a) preparing a slurry of diL-lysine monosulfate plate crystals at a temperature above approximately 40° C.,
    b) lowering the temperature until it is between approximately −10 to 35° C., and allowing crystals to form, and
    c) recovering said crystals.

24. A method of producing diL-lysine sulfate comprising
    a) concentrating an aqueous diL-lysine monosulfate trihydrate solution by evaporation, and allowing a crystal to form,
    b) recovering said crystal which is characterized by having peaks at diffraction angles 2θ of 16.6° and 17.0° in powder X-ray diffraction,
    c) drying said crystal to remove the crystal water, and
    d) collecting said diL-lysine sulfate.

* * * * *

UNITED STATES PATENT AND TRADEMARK OFFICE
CERTIFICATE OF CORRECTION

PATENT NO. : 7,553,367 B2
APPLICATION NO. : 11/423969
DATED : June 30, 2009
INVENTOR(S) : Kushiku et al.

Page 1 of 1

It is certified that error appears in the above-identified patent and that said Letters Patent is hereby corrected as shown below:

Title page item (73) should read as follows:

Assignee: Ajinomoto Co., Inc., Tokyo (JP)
           Ajinomoto U.S.A. Inc., Washington, D.C. (US)

Signed and Sealed this

Twenty-eighth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,553,367 B2
APPLICATION NO. : 11/423969
DATED : June 30, 2009
INVENTOR(S) : Kushiku et al.

It is certified that error appears in the above-identified patent and that said Letters Patent is hereby corrected as shown below:

The following claims should be amended as follows:

Col. 13 claim 1. A method of producing a diL-lysine monosulfate trihydrate crystal characterized by having peaks at diffraction angles 2θ of 16.6° and 17.0° as measured by powder X-ray diffraction comprising
   a) mixing a lysine solution with sulfuric acid at a temperature of between approximately -10° and approximately 35° C., and allowing said crystal to form, and
   b) recovering said crystal.

Col. 13 claim 6. A method of producing diL-lysine sulfate comprising
   a) mixing a lysine solution with sulfuric acid at a temperature of between approximately -10° C. and approximately 35° C., and allowing a crystal to form,
   b) recovering said crystal which is characterized by having peaks at diffraction angles 2θ of 16.6° and 17.0° in powder X-ray diffraction,
   c) drying said crystal to remove the crystal water, and
   d) collecting said diL-lysine sulfate.

Col. 13 claim 11. A method of producing a diL-lysine inonosulfate trihydrate crystal characterized by having peaks at diffraction angles 2θ of 16.6° and 17.0° in powder X-ray diffraction, comprising
   a) mixing a lysine solution with sulfuric acid at a temperature above approximately 40° C., and allowing crystals to form,
   b) lowering the temperature until it is between approximately -10° C. and approximately 35° C., and allowing crystals to form, and
   e) recovering said diL-lysine mono sulfate trihydrate crystal.

Col. 14 claim 16. The method of claim 11, wherein said diL-lysine monosulfate trihydrate crystal is characterized by having peaks at diffraction angles 2θ of 16.6° and 17.0° in powder X-ray diffraction.

Col. 14 claim 17. A method of producing a diL-lysine monosulfate trihydrate crystal characterized by having peaks at diffraction angles 2θ of 16.6° and 17.0° in powder X-ray diffraction, comprising
   a) concentrating an aqueous diL-lysine monosulfate trihydrate solution by evaporation, and allowing a crystal to form, and
   b) recovering said crystal.

Col. 14 claim 19. A method of producing a diL-lysine monosulfate trihydrate crystal characterized by having peaks at diffraction angles 2θ of 16.6° and 17.0° in powder X-ray diffraction, comprising
   a) preparing an aqueous diL-lysine monosulfate trihydrate solution at a temperature above approximately 40° C.,
   b) lowering the temperature until it is between approximately -10° C. and approximately 35° C., and allowing crystals to form, and
   c) recovering said diL-lysine monosulfate trihydrate crystal.

The following claims should be amended as follows (continued):

Col. 14 claim 21. A method of producing a diL-lysine monosulfate trihydrate crystal characterized by having peaks at diffraction angles 2θ of 16.6° and 17.0° in powder X-ray diffraction, comprising
   a) adding a poor solvent to an aqueous diL-lysine mono sulfate trihydrate solution, and allowing a crystal to form, and
   b) recovering said crystal.

Col. 14 claim 23. A method of producing a diL-lysine monosulfate trihydrate column crystal characterized by having peaks at diffraction angles 2θ of 16.6° and 17.0° in powder X-ray diffraction, comprising
   a) preparing a slurry of diL-lysine monosulfate plate crystals at a temperature above approximately 40° C.,
   b) lowering the temperature until it is between approximately -10 to 35° C., and allowing crystals to form, and
   c) recovering said crystals.

Col. 14 claim 24. A method of producing diL-lysine sulfate comprising
   a) concentrating an aqueous diL-lysine monosulfate trihydrate solution by evaporation, and allowing a crystal to form,
   b) recovering said crystal which is characterized by having peaks at diffraction angles 2θ of 16.6° and 17.0° in powder X-ray diffraction,
   c) drying said crystal to remove the crystal water, and
   d) collecting said diL-lysine sulfate.

Signed and Sealed this

Ninth Day of March, 2010

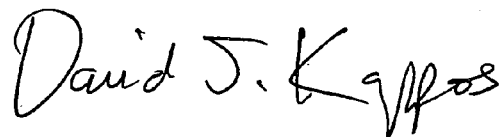

David J. Kappos
*Director of the United States Patent and Trademark Office*

UNITED STATES PATENT AND TRADEMARK OFFICE
CERTIFICATE OF CORRECTION

PATENT NO. : 7,553,367 B2
APPLICATION NO. : 11/423969
DATED : June 30, 2009
INVENTOR(S) : Kushiku et al.

It is certified that error appears in the above-identified patent and that said Letters Patent is hereby corrected as shown below:

The following claims should be amended as follows:

Col. 13, lines 12-19, claim 1. A method of producing a diL-lysine monosulfate trihydrate crystal characterized by having peaks at diffraction angles 2θ of 16.6° and 17.0° as measured by powder X-ray diffraction comprising
   a) mixing a lysine solution with sulfuric acid at a temperature of between approximately -10° and approximately 35° C., and allowing said crystal to form, and
   b) recovering said crystal.

Col. 13, lines 29-37, claim 6. A method of producing diL-lysine sulfate comprising
   a) mixing a lysine solution with sulfuric acid at a temperature of between approximately -10° C. and approximately 35° C., and allowing a crystal to form,
   b) recovering said crystal which is characterized by having peaks at diffraction angles 2θ of 16.6° and 17.0° in powder X-ray diffraction,
   c) drying said crystal to remove the crystal water, and
   d) collecting said diL-lysine sulfate.

Col. 13, lines 47-58, claim 11. A method of producing a diL-lysine inonosulfate trihydrate crystal characterized by having peaks at diffraction angles 2θ of 16.6° and 17.0° in powder X-ray diffraction, comprising
   a) mixing a lysine solution with sulfuric acid at a temperature above approximately 40° C., and allowing crystals to form,
   b) lowering the temperature until it is between approximately -10° C. and approximately 35° C., and allowing crystals to form, and
   e) recovering said diL-lysine mono sulfate trihydrate crystal.

Col. 14, lines 6-9, claim 16. The method of claim 11, wherein said diL-lysine monosulfate trihydrate crystal is characterized by having peaks at diffraction angles 2θ of 16.6° and 17.0° in powder X-ray diffraction.

Col. 14, lines 10-17, claim 17. A method of producing a diL-lysine monosulfate trihydrate crystal characterized by having peaks at diffraction angles 2θ of 16.6° and 17.0° in powder X-ray diffraction, comprising
   a) concentrating an aqueous diL-lysine monosulfate trihydrate solution by evaporation, and allowing a crystal to form, and
   b) recovering said crystal.

CERTIFICATE OF CORRECTION (continued)
U.S. Pat. No. 7,553,367 B2

The following claims should be amended as follows (continued):

Col. 14, lines 20-30, claim 19. A method of producing a diL-lysine monosulfate trihydrate crystal characterized by having peaks at diffraction angles 2θ of 16.6° and 17.0° in powder X-ray diffraction, comprising
   a) preparing an aqueous diL-lysine monosulfate trihydrate solution at a temperature above approximately 40° C.,
   b) lowering the temperature until it is between approximately -10° C. and approximately 35° C., and allowing crystals to form, and
   c) recovering said diL-lysine monosulfate trihydrate crystal.

Col. 14, lines 33-40, claim 21. A method of producing a diL-lysine monosulfate trihydrate crystal characterized by having peaks at diffraction angles 2θ of 16.6° and 17.0° in powder X-ray diffraction, comprising
   a) adding a poor solvent to an aqueous diL-lysine mono sulfate trihydrate solution, and allowing a crystal to form, and
   b) recovering said crystal.

Col. 14, lines 43-51, claim 23. A method of producing a diL-lysine monosulfate trihydrate column crystal characterized by having peaks at diffraction angles 2θ of 16.6° and 17.0° in powder X-ray diffraction, comprising
   a) preparing a slurry of diL-lysine monosulfate plate crystals at a temperature above approximately 40° C.,
   b) lowering the temperature until it is between approximately -10 to 35° C., and allowing crystals to form, and
   c) recovering said crystals.

Col. 14, lines 52-60, claim 24. A method of producing diL-lysine sulfate comprising
   a) concentrating an aqueous diL-lysine monosulfate trihydrate solution by evaporation, and allowing a crystal to form,
   b) recovering said crystal which is characterized by having peaks at diffraction angles 2θ of 16.6° and 17.0° in powder X-ray diffraction,
   c) drying said crystal to remove the crystal water, and
   d) collecting said diL-lysine sulfate.

This certificate supersedes the Certificate of Correction issued March 9, 2010.

Signed and Sealed this

Thirtieth Day of March, 2010

David J. Kappos
*Director of the United States Patent and Trademark Office*